US008100821B2

(12) United States Patent
Hjelle et al.

(10) Patent No.: US 8,100,821 B2
(45) Date of Patent: *Jan. 24, 2012

(54) LOW FRICTION DELIVERY TOOL FOR A CARDIAC SUPPORT DEVICE

(75) Inventors: Aaron J. Hjelle, Champlin, MN (US);
Louis Labrousse, Bordeaux (FR);
Robert G. Walsh, Lakeville, MN (US);
Paul Andrew Pignato, Stacy, MN (US);
Michael J. Girard, Lino Lakes, MN (US)

(73) Assignee: Mardil, Inc., Plymouth, MN (US)

( * ) Notice: Subject to any disclaimer, the term of this patent is extended or adjusted under 35 U.S.C. 154(b) by 508 days.

This patent is subject to a terminal disclaimer.

(21) Appl. No.: 12/333,045

(22) Filed: Dec. 11, 2008

(65) Prior Publication Data

US 2009/0131743 A1 May 21, 2009

Related U.S. Application Data

(63) Continuation of application No. 11/478,309, filed on Jun. 29, 2006, now abandoned.

(51) Int. Cl.
*A61F 2/00* (2006.01)
(52) U.S. Cl. ........................................................ 600/37
(58) Field of Classification Search .................. 600/37; 128/897–899
See application file for complete search history.

(56) References Cited

U.S. PATENT DOCUMENTS

| 1,682,119 | A | 8/1928 | Field |
| 1,965,542 | A | 11/1933 | Colvin, Jr. |
| 1,982,207 | A | 11/1934 | Furniss |
| 2,138,603 | A | 11/1938 | Johnson |
| 2,278,926 | A | 4/1942 | Hartwell |
| 2,376,442 | A | 5/1945 | Mehler |
| 2,992,550 | A | 7/1961 | Frith |
| 3,384,530 | A | 5/1968 | Mercer et al. |
| 3,452,742 | A | 7/1969 | Muller |
| 3,551,543 | A | 12/1970 | Mercer et al. |
| 3,587,567 | A | 6/1971 | Schiff |

(Continued)

FOREIGN PATENT DOCUMENTS

DE    3 24 524    8/1920

(Continued)

OTHER PUBLICATIONS

"Abstracts From the 68th Scientific Sessions, Anaheim Convention Center, Anaheim, California, Nov. 13-16, 1995", *American Heart Association Supplement to Circulation*, vol. 92, No. 8, Abstracts 1810-1813 (Oct. 15, 1995).

(Continued)

*Primary Examiner* — Samuel Gilbert
(74) *Attorney, Agent, or Firm* — The Nath Law Group; Laurie A. Axford

(57) ABSTRACT

A delivery device for efficiently delivering a cardiac support device of the type having a jacket. The device includes a body, a deployment mechanism and an actuating mechanism. The deployment mechanism is for releasable connection to a cardiac support device and movable within the jacket between retracted and extended states to drive the jacket between collapsed and open configurations. At least portions of the deployment mechanism within the jacket have a lubricious surface to substantially reduce friction between the jacket and a heart onto which the jacket is being positioned. The actuating mechanism moves the deployment mechanism between the retracted and extended states.

19 Claims, 14 Drawing Sheets

U.S. PATENT DOCUMENTS

| | | |
|---|---|---|
| 3,732,662 A | 5/1973 | Paxton |
| 3,768,643 A | 10/1973 | Bruno |
| 3,983,863 A | 10/1976 | Janke et al. |
| 4,048,990 A | 9/1977 | Goetz |
| 4,196,534 A | 4/1980 | Shibamoto |
| 4,403,604 A | 9/1983 | Wilkinson et al. |
| 4,428,375 A | 1/1984 | Ellman |
| 4,466,331 A | 8/1984 | Matheson |
| 4,536,893 A | 8/1985 | Parravicini |
| 4,567,900 A | 2/1986 | Moore |
| 4,630,597 A | 12/1986 | Kantrowitz et al. |
| 4,637,377 A | 1/1987 | Loop |
| 4,690,134 A | 9/1987 | Snyders |
| 4,790,850 A | 12/1988 | Dunn et al. |
| 4,821,723 A | 4/1989 | Baker, Jr. et al. |
| 4,827,932 A | 5/1989 | Ideker et al. |
| 4,834,707 A | 5/1989 | Evans |
| 4,840,626 A | 6/1989 | Linsky et al. |
| 4,878,890 A | 11/1989 | Bilweis |
| 4,932,972 A | 6/1990 | Dunn et al. |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 4,995,857 A | 2/1991 | Arnold |
| 5,042,463 A | 8/1991 | Lekholm |
| 5,057,117 A | 10/1991 | Atweh |
| 5,074,129 A | 12/1991 | Matthew |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,188,813 A | 2/1993 | Fairey et al. |
| 5,192,314 A | 3/1993 | Daskalakis |
| 5,207,725 A | 5/1993 | Pinkerton |
| 5,224,363 A | 7/1993 | Sutton |
| 5,256,132 A | 10/1993 | Snyders |
| 5,279,539 A | 1/1994 | Bohan et al. |
| 5,290,217 A | 3/1994 | Campos |
| 5,336,253 A | 8/1994 | Gordon et al. |
| 5,339,657 A | 8/1994 | McMurray |
| 5,341,815 A | 8/1994 | Cofone et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,405,360 A | 4/1995 | Tovey |
| 5,409,703 A | 4/1995 | McAnalley et al. |
| 5,429,584 A | 7/1995 | Chiu |
| 5,507,779 A | 4/1996 | Altman |
| 5,524,633 A | 6/1996 | Heaven et al. |
| 5,533,958 A | 7/1996 | Wilk |
| 5,558,617 A | 9/1996 | Heilman et al. |
| 5,593,441 A | 1/1997 | Lichtenstein et al. |
| 5,603,337 A | 2/1997 | Jarvik |
| 5,611,515 A | 3/1997 | Benderev et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,735,290 A | 4/1998 | Sterman et al. |
| 5,766,216 A | 6/1998 | Gangal et al. |
| 5,782,746 A | 7/1998 | Wright |
| 5,800,334 A | 9/1998 | Wilk |
| 5,800,528 A | 9/1998 | Lederman et al. |
| 5,839,842 A | 11/1998 | Wanat et al. |
| 5,853,422 A | 12/1998 | Huebsch et al. |
| 5,928,250 A | 7/1999 | Koike et al. |
| 5,931,810 A | 8/1999 | Grabek |
| 5,961,440 A | 10/1999 | Schweich, Jr. et al. |
| 5,972,013 A | 10/1999 | Schmidt |
| 5,990,378 A | 11/1999 | Ellis |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,085,754 A | 7/2000 | Alferness et al. |
| 6,089,051 A | 7/2000 | Gorywoda et al. |
| 6,095,968 A | 8/2000 | Snyders |
| 6,123,662 A | 9/2000 | Alferness et al. |
| 6,126,590 A | 10/2000 | Alferness |
| 6,155,968 A | 12/2000 | Wilk |
| 6,155,972 A | 12/2000 | Nauertz et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,193,648 B1 | 2/2001 | Krueger |
| 6,205,747 B1 | 3/2001 | Paniagua Olaechea |
| 6,206,004 B1 | 3/2001 | Schmidt et al. |
| 6,224,540 B1 | 5/2001 | Lederman et al. |
| 6,230,714 B1 | 5/2001 | Alferness et al. |
| 6,241,654 B1 | 6/2001 | Alferness |
| 6,293,906 B1 * | 9/2001 | Vanden Hoek et al. ......... 600/37 |
| 6,360,749 B1 | 3/2002 | Jayaraman |
| 6,370,429 B1 | 4/2002 | Alferness et al. |
| 6,375,608 B1 | 4/2002 | Alferness |
| 6,402,680 B2 | 6/2002 | Mortier et al. |
| 6,416,459 B1 | 7/2002 | Haindl |
| 6,425,856 B1 | 7/2002 | Shapland et al. |
| 6,432,039 B1 | 8/2002 | Wardle |
| 6,482,146 B1 | 11/2002 | Alferness et al. |
| 6,508,756 B1 | 1/2003 | Kung et al. |
| 6,517,570 B1 | 2/2003 | Lau et al. |
| 6,537,203 B1 | 3/2003 | Alferness et al. |
| 6,541,678 B2 | 4/2003 | Klein |
| 6,544,168 B2 | 4/2003 | Alferness |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 | 9/2003 | Taheri |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,689,048 B2 | 2/2004 | Vanden Hoek et al. |
| 6,695,769 B2 | 2/2004 | French et al. |
| 6,702,732 B1 | 3/2004 | Lau et al. |
| 6,723,041 B2 | 4/2004 | Lau et al. |
| 6,727,316 B1 | 4/2004 | Bremser |
| 6,730,016 B1 | 5/2004 | Cox et al. |
| 6,755,779 B2 | 6/2004 | Vanden Hoek et al. |
| 6,881,185 B2 | 4/2005 | Vanden Hoek et al. |
| 6,893,392 B2 | 5/2005 | Alferness |
| 6,902,522 B1 | 6/2005 | Walsh et al. |
| 6,902,524 B2 | 6/2005 | Alferness et al. |
| 6,908,426 B2 | 6/2005 | Shapland et al. |
| 6,951,534 B2 | 10/2005 | Girard |
| 7,060,023 B2 | 6/2006 | French et al. |
| 7,081,086 B2 | 7/2006 | Lau et al. |
| 7,155,295 B2 | 12/2006 | Lau et al. |
| 7,163,507 B2 | 1/2007 | Alferness et al. |
| 7,189,203 B2 | 3/2007 | Lau et al. |
| 7,235,042 B2 | 6/2007 | Vanden Hoek et al. |
| 7,252,632 B2 | 8/2007 | Shapland et al. |
| 7,398,781 B1 | 7/2008 | Chin |
| 7,651,462 B2 * | 1/2010 | Hjelle et al. ................... 600/37 |
| 2002/0019580 A1 | 2/2002 | Lau et al. |
| 2002/0133055 A1 | 9/2002 | Haindl |
| 2003/0060895 A1 | 3/2003 | French et al. |
| 2003/0229260 A1 | 12/2003 | Girard et al. |
| 2004/0059181 A1 | 3/2004 | Alferness |
| 2004/0210104 A1 | 10/2004 | Lau et al. |
| 2005/0033109 A1 | 2/2005 | Lau et al. |
| 2005/0059854 A1 | 3/2005 | Vanden Hoek et al. |

| | | | |
|---|---|---|---|
| 2005/0059855 A1 | 3/2005 | Lau et al. |
| 2005/0090707 A1 | 4/2005 | Lau et al. |
| 2005/0171589 A1 | 8/2005 | Lau et al. |
| 2005/0192474 A1 | 9/2005 | Vanden Hoek et al. |
| 2005/0256368 A1 | 11/2005 | Klenk et al. |
| 2005/0288715 A1 | 12/2005 | Lau et al. |
| 2006/0009831 A1 | 1/2006 | Lau et al. |
| 2006/0229490 A1 | 10/2006 | Chin |
| 2006/0270896 A1 | 11/2006 | Dietz et al. |
| 2007/0208211 A1 | 9/2007 | Alferness et al. |
| 2007/0208215 A1 | 9/2007 | Hjelle |
| 2007/0219407 A1 | 9/2007 | Vanden Hoek et al. |
| 2007/0225547 A1 | 9/2007 | Alferness et al. |

FOREIGN PATENT DOCUMENTS

| | | |
|---|---|---|
| DE | 38 31 540 | 4/1989 |
| DE | 295 17 393 | 3/1996 |
| EP | 0 280 564 | 8/1988 |
| EP | 0 303 719 | 2/1989 |
| EP | 0 557 964 | 9/1993 |
| GB | 2 209 678 | 5/1989 |
| JP | 60-203250 | 10/1985 |
| JP | 01-145066 | 6/1989 |
| JP | 2-271829 | 11/1990 |
| SU | 1009457 | 4/1983 |
| WO | WO 93/03685 | 3/1993 |
| WO | WO 96/16601 | 6/1996 |
| WO | WO 96/31175 | 10/1996 |
| WO | WO 98/14136 | 4/1998 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/01306 | 1/2000 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/02500 | 1/2001 |
| WO | WO 01/67985 | 9/2001 |
| WO | WO 2006/023580 | 3/2006 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", *American Heart Journal*, pp. 1089-1098 (Dec. 1997).

Capouya et al., "Girdling Effect of Nonstimulated Cardiomyoplasty on Left Ventricular Function", *The Society of Thoracic Surgeons*, vol. 56, pp. 867-871 (1993).

Cohn, "The Management of Chronic Heart Failure", *The New England Journal of Medicine*, vol. 335, No. 7, pp. 490-498 (Aug. 15, 1996).

Colleta et al., "Prognostic value of left ventricular volume response during dobutamine stress echocardiography", *European Heart Journal*, vol. 18, pp. 1599-1605 (Oct. 1997).

deVries, G. et al., "A Novel Technique for Measurement of Pericardial Balloon," *Am. J. Physiol Heart Circ Physiol*, vol. 280, No. 6, pp. H2815-H2822 (Jan. 2001).

Guasp, "Una protesis contentiva para el tratamiento de la miocardiopatia dilatada" *Revista Espanola de Cardiologia*, vol. 51, No. 7, pp. 521-528 (1998). (Includes the English translation).

Hamilton, D. et al., "Static and Dynamic Operating Characteristics of a Pericardial Balloon," *J. Appl. Physiol*, vol. 90, No. 4, pp. 1481-1488 (Apr. 2001).

Kass et al., "Reverse Remodeling From Cardiomyoplasty in Human Heart Failure", *Circulation*, vol. 91, No. 9, pp. 2314-2318 (May 1, 1995).

Labrousse, Louis et al., "Implantation of a Cardiac Support Device by the 'Parachute-Like' Technique Through Sternal and Trans-Abdominal Approach", Abstract, 94 Programme of the 4th EACTS/ESTS Joint Meeting, Wednesday Sep. 28, 2005, Barcelona, Spain.

Levin et al., "Reversal of Chronic Ventricular Dilation in Patients With End-Stage Cardiomyopathy by Prolonged Mechanical Unloading", *Circulation*, vol. 91, No. 11, pp. 2717-2720 (Jun. 1, 1995).

Oh et al., "The Effects of Prosthetic Cardiac Binding and Adynamic Cardiomyoplasty in a Model of Dilated Cardiomyopathy", *The Journal of Thoracic and Cardiovascular Surgery*, vol. 116, No. 1, pp. 148-153 (Jul. 1998).

Paling, "Two-Bar Fabrics (Part-Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64 (1997).

Vinereanu, et al., "Worsening Global Diastolic Dysfunction of the Left Ventricle is Associated with a Progressive Decline in Longitudinal Systolic Function", *European Journal of Heart Failure*, Aug. 7(5): 820-8 (2005).

U.S. Appl. No. 60/148,130 entitled, "Apparatus and Method for Endoscopic Pericardial Access", filed Aug. 10, 1999.

U.S. Appl. No. 60/150,737 entitled, "Longitudinal Mechanical Dilator for Vessel Harvesting", filed Aug. 25, 1999.

Office Action mailed Jun. 11, 2008 in U.S. Appl. No. 11/478,309, 8 pages.

International Search Report and Written Opinion from international application No. PCT/US2007/072345, mailed Jul. 3, 2008, 9 pages.

European Search Report dated Dec. 2, 2009 for EP Application No. 07799122, 9 pages.

Non-Final Office Action mailed Dec. 11, 2009 in U.S. Appl. No. 11/478,350, 8 pages.

Non-Final Office Action mailed Dec. 11, 2009 in U.S. Appl. No. 11/478,311, 8 pages.

\* cited by examiner

LOW FRICTION DELIVERY TOOL FOR A CARDIAC SUPPORT DEVICE

REFERENCE TO RELATED APPLICATION

This application is a continuation of U.S. Ser. No. 11/478,309, filed Jun. 29, 2006, entitled "LOW FRICTION DELIVERY TOOL FOR A CARDIAC SUPPORT DEVICE," which is incorporated herein by reference.

FIELD OF THE INVENTION

The invention is a device for deploying a cardiac support device on a patient's heart.

BACKGROUND OF THE INVENTION

Cardiac support devices are structures, sometimes referred to as jackets, that surround all or portions of a diseased heart. These devices are intended to treat chronic heart failure or other cardiac disease, which may be associated valvular dysfunction, by constraining expansion of the heart. They can be delivered and implanted using conventional cardiothoracic surgical techniques or minimally invasive surgical procedures. Devices of these types and associated delivery tools and methods are shown, for example, in the following U.S. patents, all of which are incorporated herein by reference in their entirety.

| Inventor Name | Patent/Publication No. |
| --- | --- |
| Alferness | 5,702,343 |
| Alferness et al. | 6,123,662 |
| Vanden Hoek et al. | 6,293,906 |
| Alferness et al. | 6,482,146 |
| Lau et al. | 6,702,732 |
| Cox et al. | 6,730,016 |
| Walsh et al. | 6,902,522 |
| Girard et al. | 6,951,534 |

During the delivery procedures portions of the cardiac support devices sometimes encounter frictional resistance on the heart surface during placement. There is, therefore, a continuing need for improved devices for use during the delivery of cardiac support devices. An invention of this type that can enhance the efficiency of the delivery procedure would be especially desirable.

SUMMARY OF THE INVENTION

The present invention is an improved delivery device for use in connection with cardiac support devices having jackets. Cardiac support devices can be efficiently implanted within a patient using these devices. One embodiment of the device includes a body, a deployment mechanism and an actuating mechanism. The deployment mechanism is for releasable connection to a cardiac support device and movable within the jacket between retracted and extended states to drive the jacket between collapsed and open configurations. At least portions of the deployment mechanism within the jacket have a lubricious surface to substantially reduce friction between the jacket and a heart onto which the jacket is being positioned. The actuating mechanism moves the deployment mechanism between the retracted and extended states.

DETAILED DESCRIPTION OF THE PREFERRED EMBODIMENTS

Figure 1:
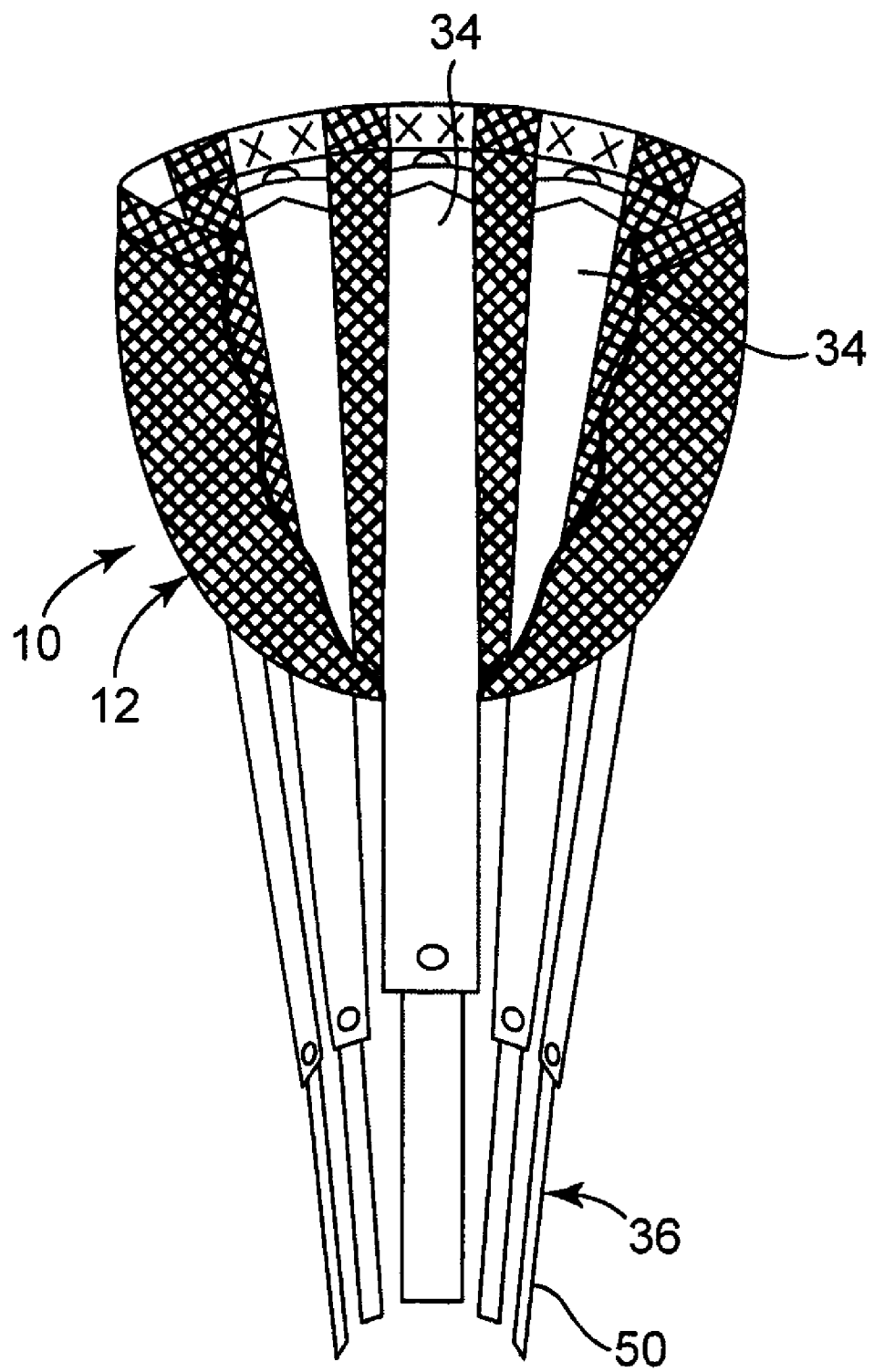
FIG. 1 is an isometric side view of a cardiac support device in accordance with one embodiment of the present invention, with portions thereof broken away to illustrate the lubricious element assemblies.
Figure 2:
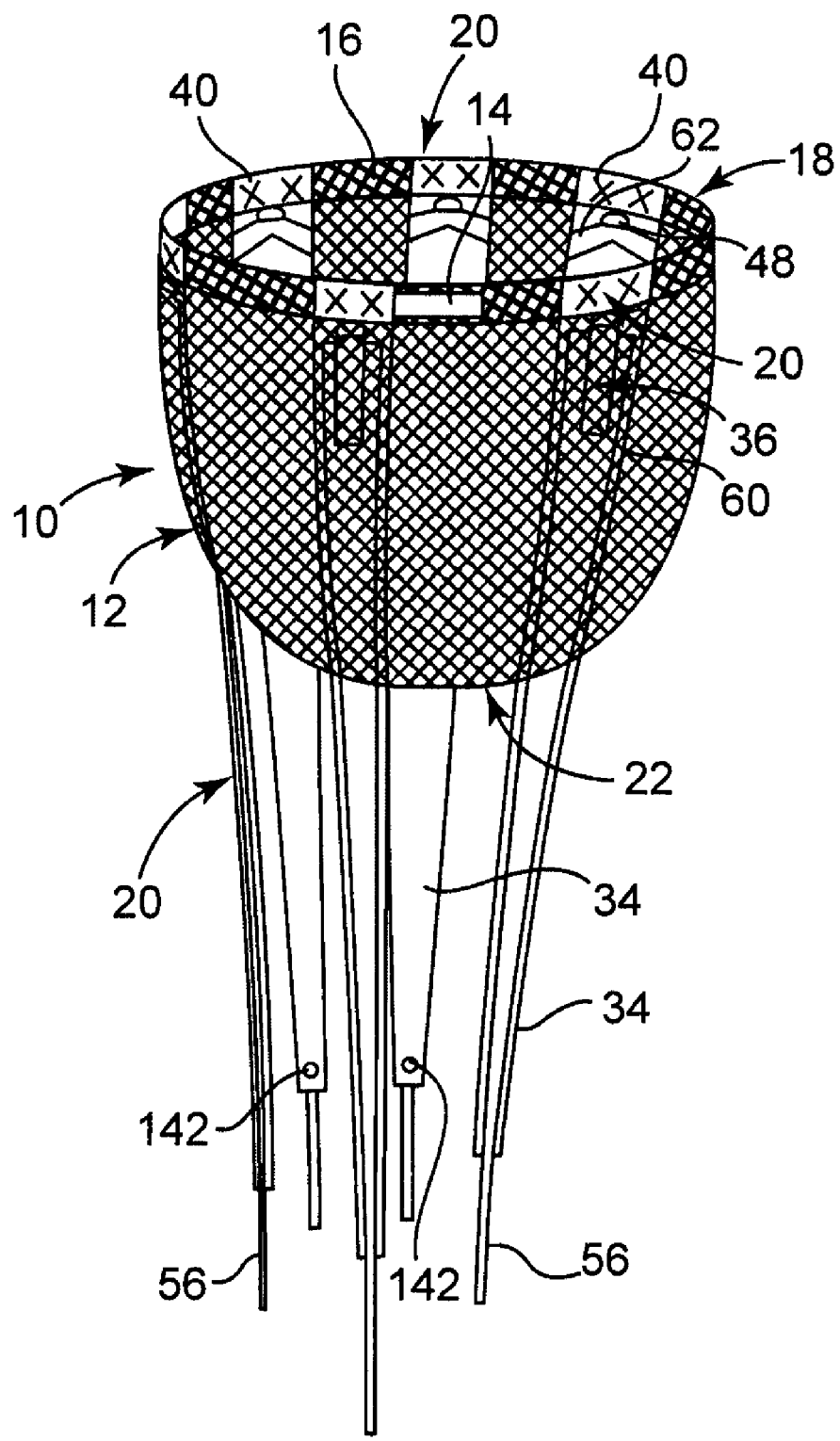
FIG. 2 is an isometric side view of the cardiac support device shown in FIG. 1, illustrating the side of the device opposite that shown in FIG. 1.

FIGS. 1 and 2 are illustrations of the opposite sides of a cardiac support device (CSD) 10 in accordance with one embodiment of the invention. As shown, CSD 10 includes a jacket 12, a self-adjusting securing structure in the form of an elastic band 14 in a hem 16 on the base end 18 of the jacket, and a plurality of lubricious element assemblies 20. The illustrated embodiment of jacket 12 is generally conical and has an apex end 22 opposite the base end 18. Both the base end 18 and apex end 22 are open to permit access to the internal volume of the jacket 12.

Lubricious element assemblies 20 are attached to the jacket 12 near the base end 18, extend along the inside surface of the jacket, and extend through and beyond the open apex end 22. Although CSD 10 includes six lubricious element assemblies 20 in the illustrated embodiment, other embodiments (not shown) include more or fewer such assemblies. As described in greater detail below, the lubricious element assemblies 20 facilitate the deployment or positioning of CSD 10 on a patient's heart by providing a lubricious (i.e., relatively low friction) interface between at least portions of the inside surface of the jacket 12 and the epicardial (or other) surface of the heart while the CSD is being slid onto the heart. After deployment of the CSD 10, all or portions of the lubricious element assemblies are removed from the CSD and patient.

Jacket 12 and/or the securing structure can be similar or identical to those described in any of the following U.S. patents and applications assigned to Acorn Cardiovascular, Inc., all of which are incorporated herein by reference: U.S. Pat. Nos. 5,702,343; 6,155,972; 6,193,648; 6,482,146; 6,682, 476; 6,902,524; 6,425,856; 6,908,426; 6,572,533; 6,673,009; 6,951,534; and application Ser. No. 11/367,759, filed Mar. 3, 2006, and entitled Self-Adjusting Securing Structure For A Cardiac Support Device. In still other embodiments the jacket 12 can be similar or identical to those described in U.S. Pat. Nos. 6,702,732 and 6,723,041, both of which are assigned to Paracor and are incorporated herein by reference. In one embodiment, the material of jacket 12 can be an open-cell construction of a polyester knit material as more fully described in U.S. Pat. No. 6,482,146. In yet another embodiment, the material of jacket 12 can be an open-cell construction of a polyester knit material as more fully described in U.S. Pat. No. 6,951,534. These examples of jacket 12 and the securing structure are not limiting. Other jackets 12 and securing structures and methods can also be used. Furthermore, the apex end 22 can be an open or closed apex.

Figure 3A:
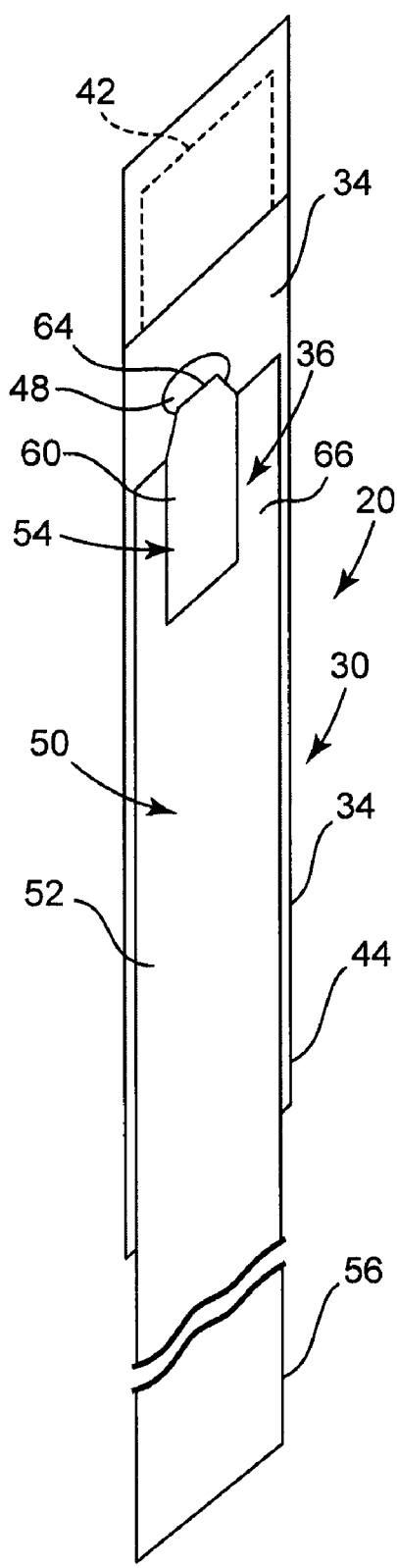
FIGS. 3A and 3B are detailed illustrations of the opposite sides of the lubricious element assemblies shown in FIGS. 1 and 2, in an unreleased state.
Figure 3B:
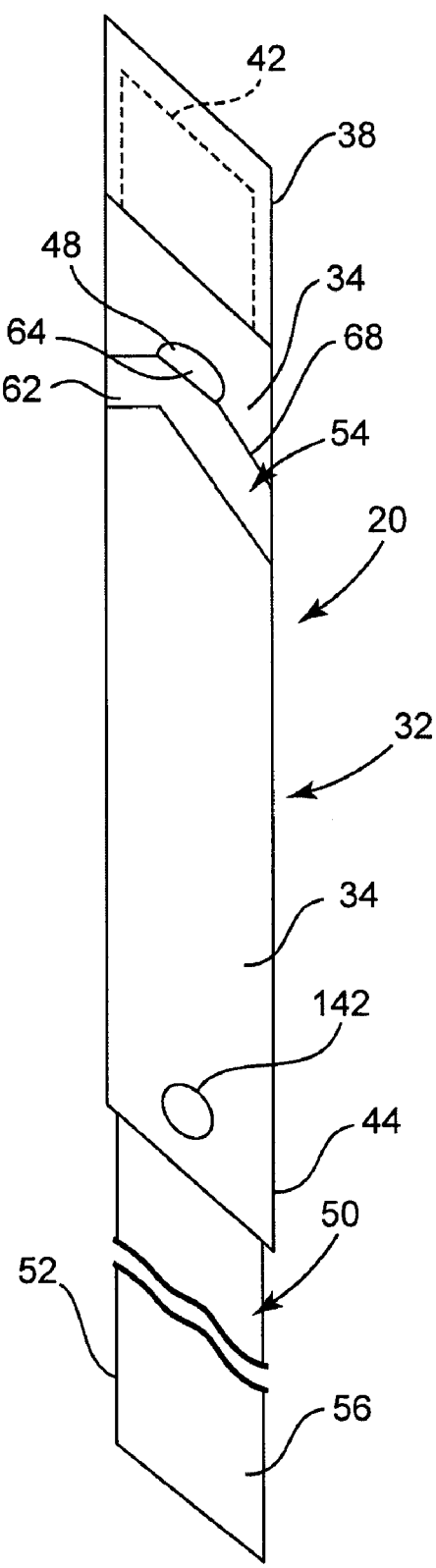

FIGS. 3A and 3B are illustrations of the removal member side 30 and opposite lubricious member side 32 of one of the lubricious element assemblies 20. As shown, the lubricious element assemblies 20 include a lubricious member 34 and a removal member 36. Lubricious member 34 has a relatively low friction surface on at least the lubricious member side 32 of the assembly 20 (i.e., on the side of the member that will engage the heart when the CSD 10 is placed on the heart). In the illustrated embodiment, the lubricious member 34 is a flexible strip of PTFE (i.e., fluorinated polymer) sheet material. Both of the entire surfaces of this PTFE lubricious member 34 therefore have a low friction surface. In other embodiments (not shown) the lubricious member 34 can take other forms. Lubricious member 34 can, for example, be high density polyethylene, low density polyethylene, ultra high molecular weight polyethylene, Rulon™ co-polymer, graphite doped polymer and polymer impregnated with lubricious materials. Alternatively or in addition, lubricious members can have a substrate of any of the materials described above, or other materials including non-lubricious materials, with all or portions of their opposite surfaces coated with relatively low friction material. Non-limiting examples of lubricious coatings that can be used with the invention include hydrophilic and hydrophobic coatings such as hyaluronic acid, polyethylene glycol, PTFE and silicone. In yet other embodiments of the invention, the lubricious surface portions are provided by materials or coatings that may not themselves be relatively low friction, but have relatively low friction characteristics when wet by liquids. Hydrogels are one example of materials of these types. By way of example only, the member 34 can be a sheet of polymer or other material having low-friction coatings on all or portions of its opposite surfaces. The size (e.g., the length and width) of the lubricious members 34 can also be different that those shown and described herein. For example, the lubricious members 34 can be sized to line all or substantially all of the inside surface of the jacket 12.

An upper portion 38 of the lubricious member 34 is attached to the jacket 12. In the embodiment shown, the upper portion 38 of lubricious member 34 includes a folded section that extends over the base end 18 of the jacket 12. Stitches 40 can be used to attach the upper portion 38 of lubricious member 34 to the jacket 12. In other embodiments (not shown) the lubricious element assemblies 20 can be attached to other portions of jacket 12, and other structures or methods (e.g., adhesives) can be used to secure the assemblies or lubricious members such as 34 to the jacket. A pocket 42 is also formed in the upper portion 38 of lubricious member 34. Pocket 42 opens toward a lower portion 44 of the lubricious member 34 on the lubricious member side 32 of the assembly 20. As described below, pocket 42 is used to mount the CSD 10 to a delivery tool for deployment of the CSD.

Removal member 36 is operated to remove the lubricious member 34 from the jacket 12 following the positioning of the CSD 10 on the heart. In the embodiment shown, the removal member 36 includes an actuating member 50 connected to the lubricious member 34. The removal member 36 cooperates with a hole 48 through the lubricious member 34 that functions as a weakening structure. The actuating member 50 includes a pull member 52 and a tear member 54 in the embodiment shown. Pull member 52 is an elongated member having a proximal end 56 that can be accessed by a surgeon. In one embodiment the pull member 52 is an elongated strip of PTFE material. Although the use of this low friction material in this application provides advantages such as enhanced friction reduction, other structures (e.g., other materials, strings or wires; not shown) can also be used. Tear member 54 connects a distal end 58 of the pull member 52 to the lubricious member 34 near the weakening structure. In the embodiment shown, the tear member 54 is a thin metal member having an attachment portion 60 and tear strip 62 joined by a connecting portion 64. The attachment portion 60 is attached (e.g., by adhesive) to the distal end 66 of pull member 52. Connecting portion 64 extends through the hole 48. Tear strip 62 is attached to the lubricious member 34 (e.g., by adhesive) and includes edges 68 that extend at an angle to the sides of the lubricious member.

Figure 4A:
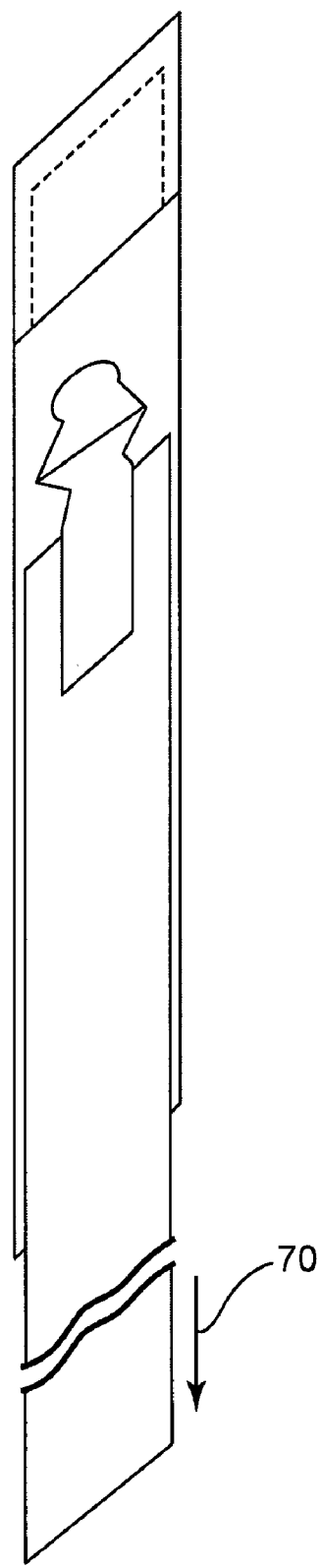
FIGS. 4A and 4B are illustrations of the opposite sides of the lubricious element assemblies shown in FIGS. 3A and 3B, in a partially released state.
Figure 4B:
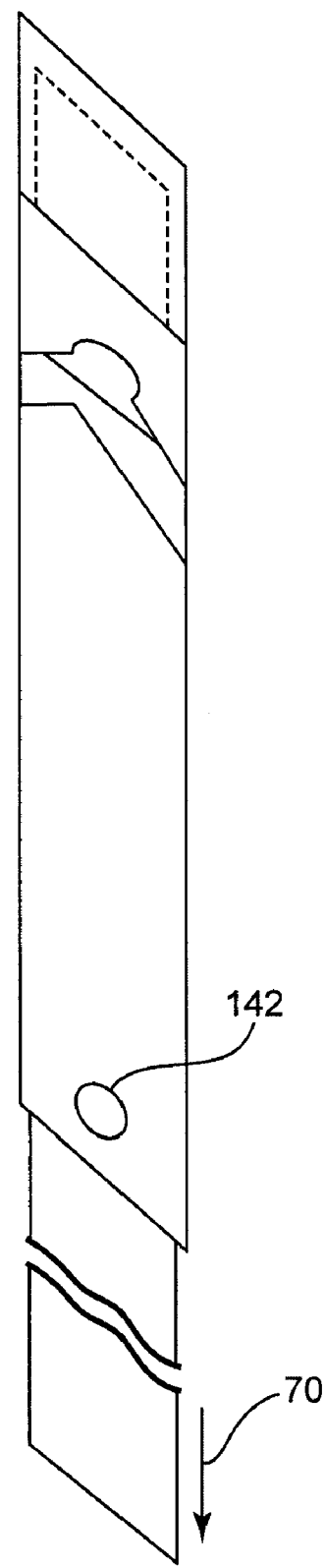
Figure 5A:
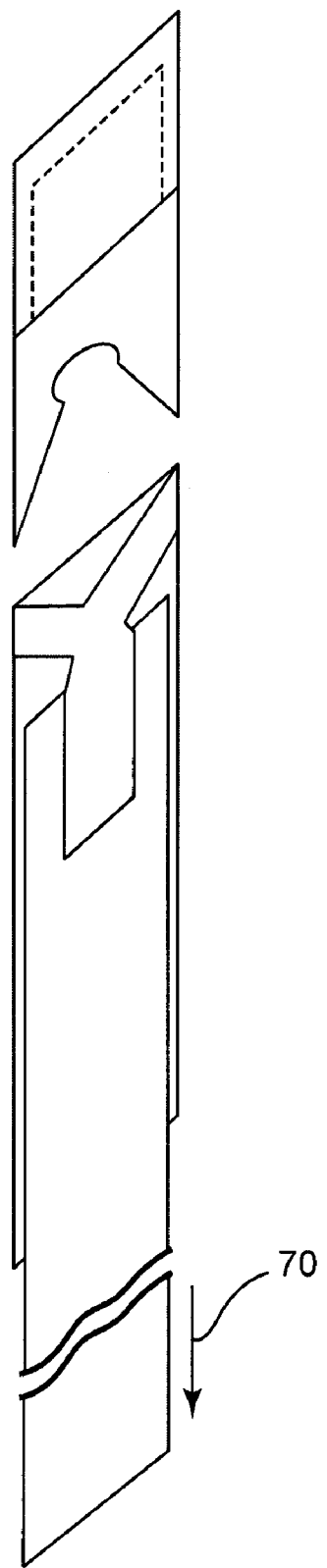
FIGS. 5A and 5B are illustrations of the opposite sides of the lubricious element assemblies shown in FIGS. 3A and 3B, in a fully released state.
Figure 5B:
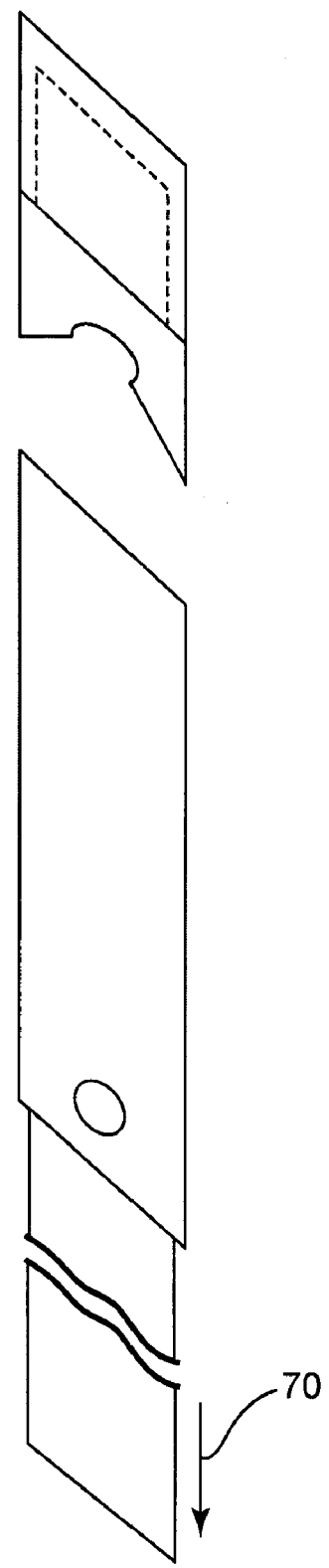

The operation of removal member 36 to release and remove the lubricious member 34 (and the removal member) from the CSD 10 can be described with reference to FIGS. 4A, 4B, 5A and 5B. As will be described below, the base end 18 of the jacket 12 and the upper portion 38 of the lubricious member 34 will be engaged during the removal process by a member extending into the pocket 42. With the base end 18 of the jacket 12 supported in this manner, a surgeon or other clinician will engage the pull member 52 (e.g., near its proximal end 56) by hand or using an instrument, and pull the pull member in a direction 70 generally away from the upper portion 38 of the lubricious member 34. This action will cause the edges 68 of the tear strip 62 to sever the lubricious member 34, starting at the hole 48. FIGS. 4A and 4B show the portion of the lubricious member 34 below the hole 48 partially severed from the portion of the member above the hole. With continued actuation of the pull member 52 this action will cause the portion of the lubricious member 34 below the hole 48 to be completely severed from the portion of the member above the hole as shown in FIGS. 5A and 5B.

Figure 6:
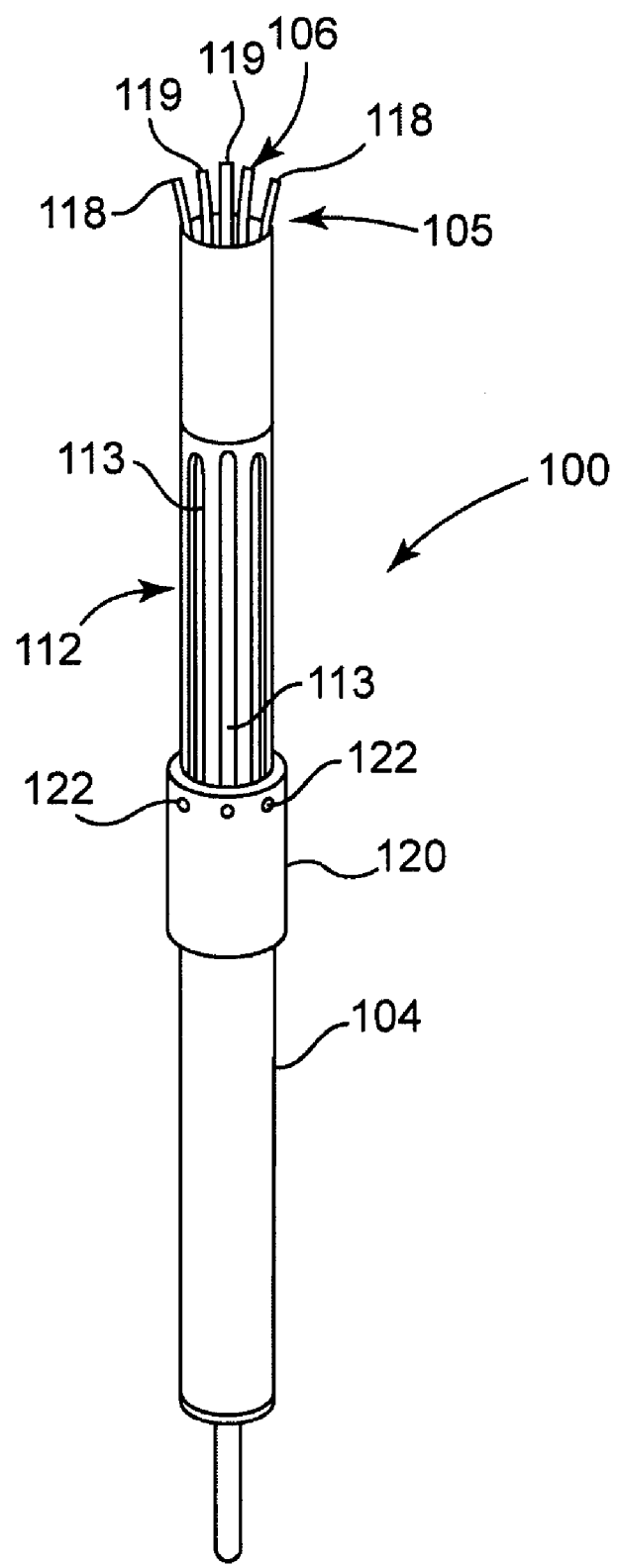
FIG. 6 is an isometric view of a delivery device in accordance with one embodiment of the invention, shown in a retracted state, that can be used to position the cardiac support device shown in FIG. 1 on a patient's heart.
Figure 7:
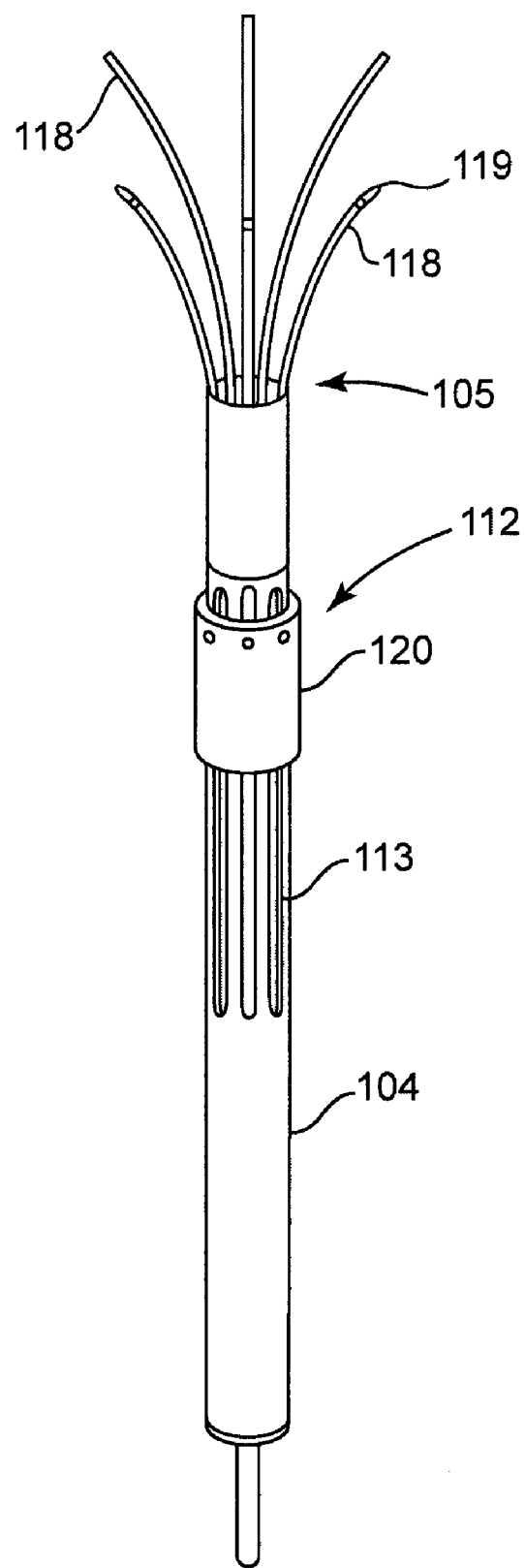
FIG. 7 is an isometric view of the delivery device shown in FIG. 6, shown in an extended state.

FIGS. 6 and 7 illustrate a delivery device 100 in accordance with one embodiment of the invention that can be used to deliver and deploy or position the CSD 10 on the heart of a patient. The delivery device 100 includes a body 104 having a distal end 105, a deployment mechanism 106 and an actuating mechanism 112. The body 104 is a generally tubular member, and includes a plurality of elongated slots 113 (six are shown in the illustrated embodiment) extending through the body at a location adjacent to the actuating mechanism 112. Actuating mechanism 112 includes a handle 120 that is slidably mounted to the body 104. Structures such as pins 122 on the handle 120 extend into the slots 113. Deployment mechanism 106 includes a plurality (six are shown) of support members 118 within the body 104. Proximal ends (not visible) of each of the support members 118 are connected to the pins 122 within the body 104. The distal portions 119 of the support members 118 are located near the distal end 105 of the body 104. Other embodiments of delivery device 100 (not shown) include a suction cup connected to a vacuum source or other structure for releasably engaging the distal end 105 of the body 104 to the heart during delivery procedures.

Handle 120 is actuated to drive the deployment mechanism 106 between a first retracted or closed state shown in FIG. 6 and a second extended or open state shown in FIG. 7. In the retracted state shown in FIG. 6, the support members 118 are in a reduced-diameter configuration. In the illustrated embodiment this configuration is achieved by the handle withdrawing at least portions of the support members 118 into the distal end 105 of the body 104. Distal end portions 119 of the support members 118 extend from the body 104 in the illustrated embodiment when the deployment mechanism 106 is in the retracted state. When the handle 120 is slid toward the distal end 105 of the body 104, the support members 118 are driven to the extended state shown in FIG. 7 at which the distal ends form an open array or enlarged-diameter configuration.

Support members 118 can be resilient structures formed from polymer, metal or other materials. For example, the members 118 (or portions thereof) can be formed of PTFE or other materials having low friction characteristics or coatings. The members 118 can also be preshaped so that they assume the open array configuration shown in FIG. 7 when the deployment mechanism 106 is in the extended state. These resilient support members 118 will be urged into the reduced diameter configuration by the body 104 when the deployment mechanism 106 is moved to the retracted state. In other embodiments, other structures (not shown) are used to cause the deployment mechanism to move between the retracted and extended states.

Figure 8:
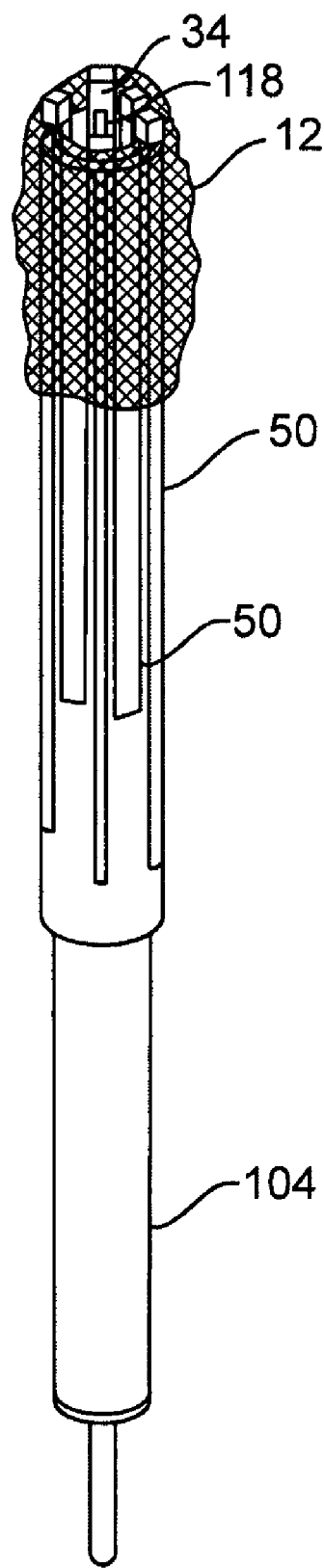
FIG. 8 is an isometric view of the delivery device shown in FIGS. 6 and 7, shown in the retracted state with the cardiac support device shown in FIGS. 1 and 2 loaded thereon.
Figure 9:
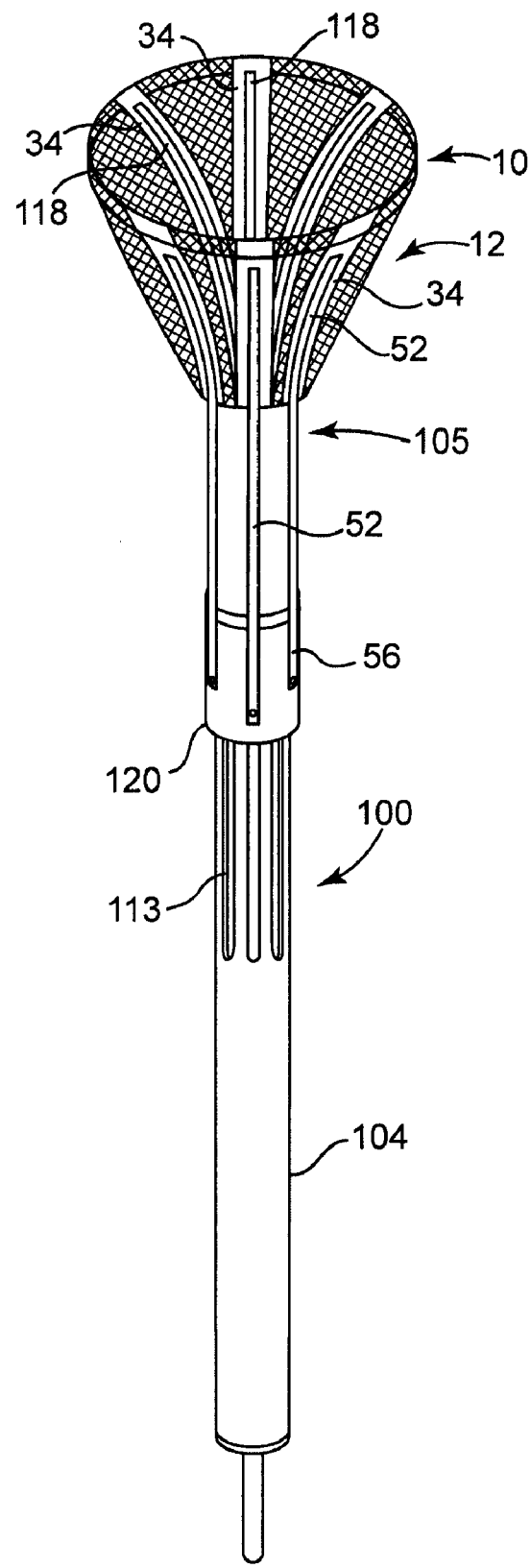
FIG. 9 is an isometric view of the delivery device and loaded cardiac support device shown in FIG. 8, shown in the extended state.
Figure 10A:
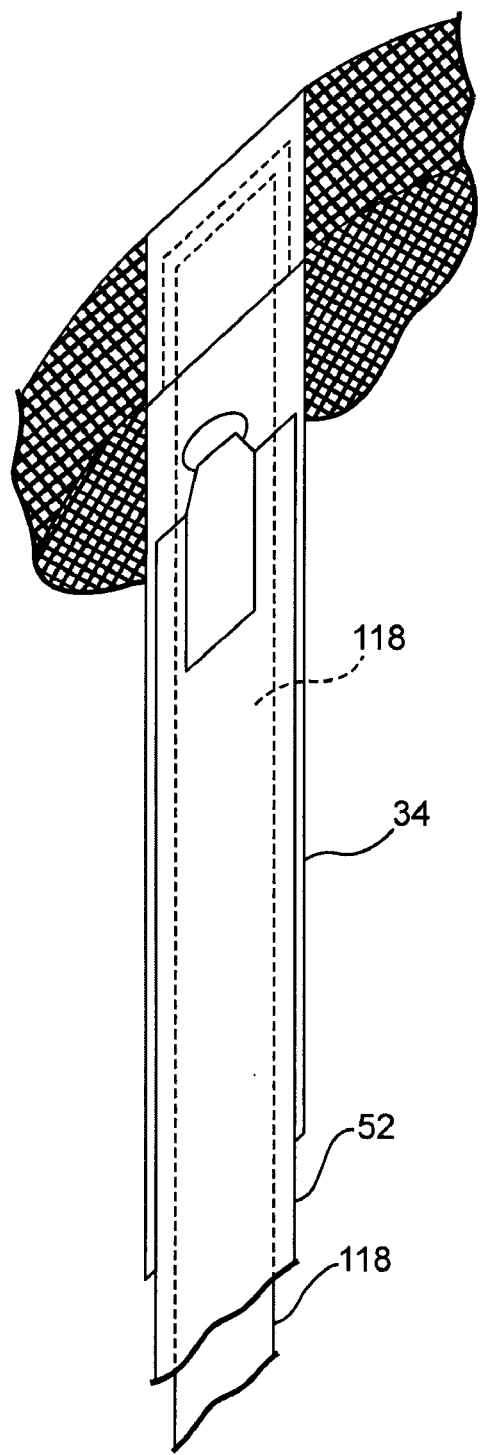
FIGS. 10A and 10B are detailed illustrations of the opposite sides of a portion of the delivery device and loaded cardiac support device shown in FIGS. 8 and 9, showing the distal end of the delivery device support member extending into a pocket in an upper section of a lubricious member.
Figure 10B:
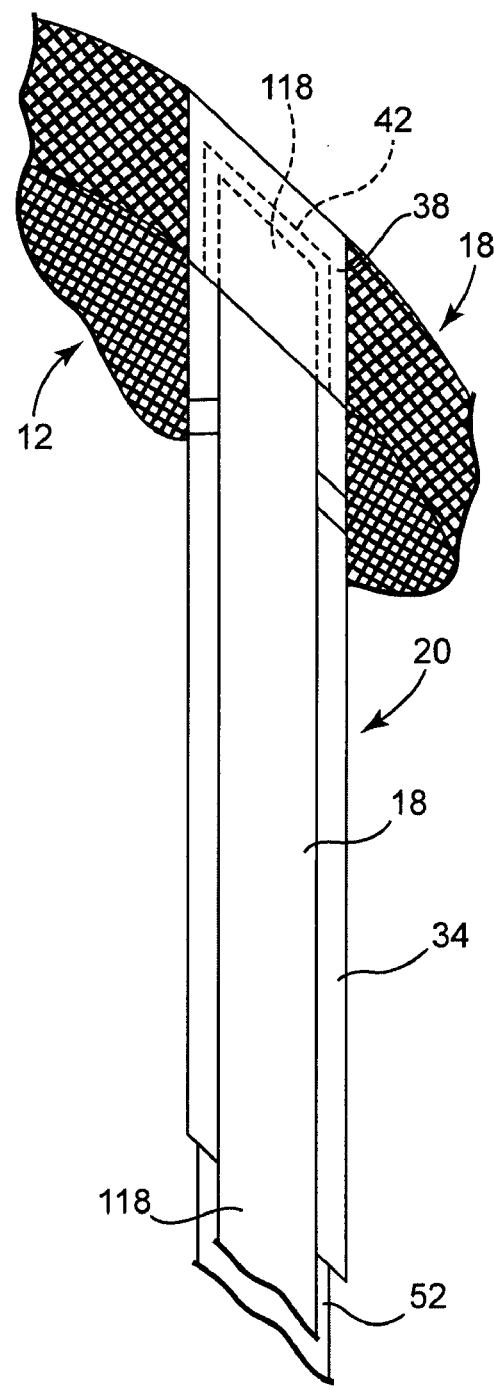

FIG. 8 is an illustration of the CSD 10 mounted or loaded on the delivery device 100, with the deployment mechanism 106 in the retracted state. FIG. 9 is an illustration of the delivery device 100 with the CSD 10 loaded thereon, with the deployment mechanism 106 in the extended state. As perhaps best shown in FIGS. 10A and 10B, in the illustrated embodiment the base end 18 of CSD 10 is releasably mounted to the delivery device 100 by inserting the distal end portions 119 of the support members 118 into the pockets 42 of the lubricious element assemblies 20. Other structures or methods (not shown) can also be used to releasably secure the CSD 10 and/or the upper or distal portions of the lubricious element assemblies 20 to the support members 118 of the deployment mechanism 106. Although the illustrated embodiment of delivery device 100 is configured to receive the CSD 10 on the outside of the body 104 when in the retracted state, the CSD can be partially or fully enclosed within the body or other structures of the delivery device in other embodiments (not shown).

Figure 11:
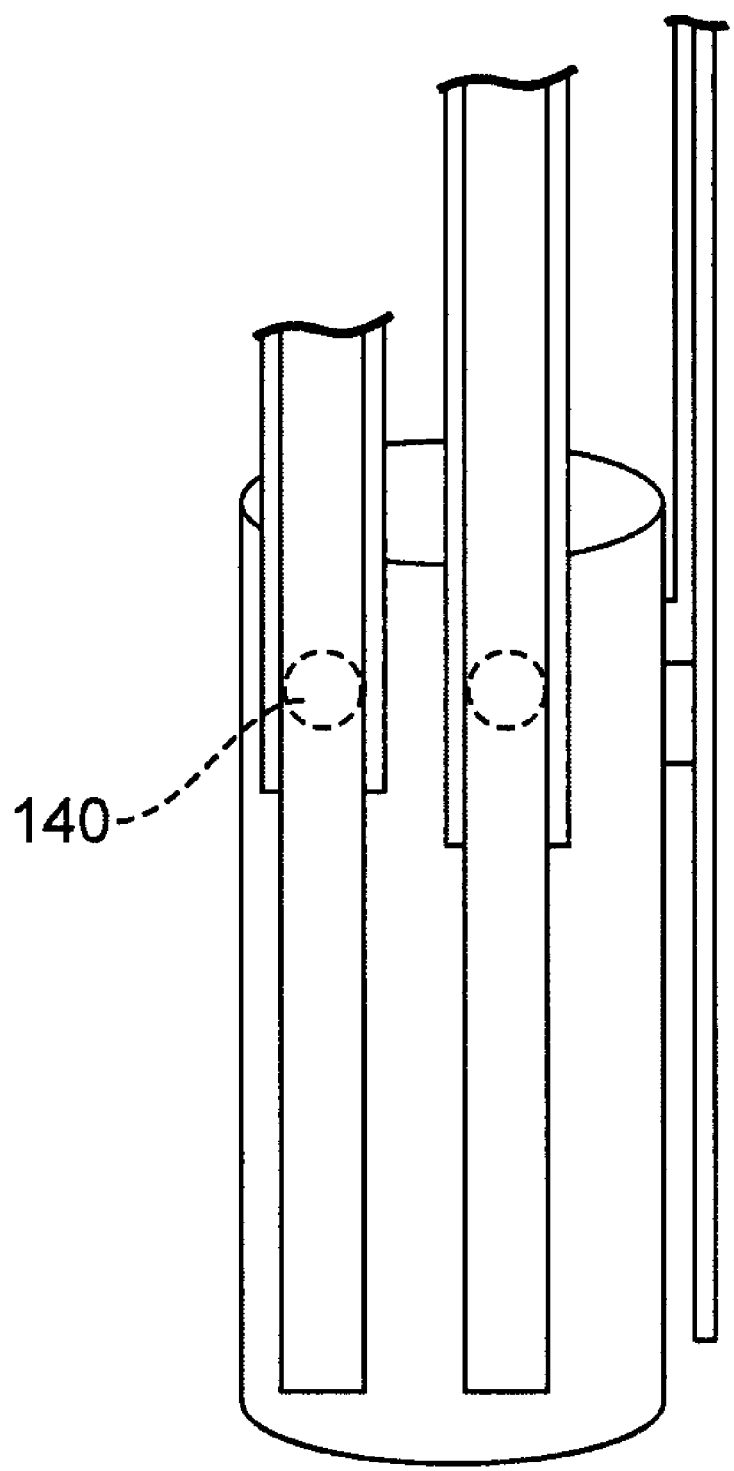
FIG. 11 is a detailed illustration of a portion of the delivery device and loaded cardiac support device shown in FIGS. 8 and 9, showing the handle of the delivery device and the lubricious members of the lubricious element assemblies releasably attached thereto.

As perhaps best shown in FIG. 11, the lower portions 44 of the lubricious members 34 are releasably secured to the handle 120. The illustrated embodiment of the invention includes a plurality of pins 140 (one for each lubricious member 34) extending from the handle 120 at circumferentially-spaced locations. The lower portions 44 of the lubricious members 34 include structures such as holes 142 that can engage the pins 140. Other structures or methods (not shown) can be used to releasably secure the lubricious members 34 to the delivery device 100. In still other embodiments of the invention (not shown) the proximal ends of the lubricious members 34 are not releasably secured to the delivery device 100.

In the retracted state shown in FIG. 8, the deployment mechanism 106 causes the CSD 10 to be in a collapsed state adjacent to the exterior surface of the body 104. The base end 18 of the jacket 12 is engaged with the distal end portions 119 of the support members 118, and the lower portions 44 of the lubricious members 34 are engaged with the handle 120. The opposite ends of the CSD 10 are therefore effectively constrained, preventing substantial movement of the CSD with respect to the delivery device 100 along the longitudinal axis of the delivery device. The delivery device 100 can then be manipulated to insert the distal end of the delivery device and the CSD 10 mounted thereon into the pericardial space of a patient (not shown) through a relatively small incision using minimally invasive surgical procedures. The delivery device 100 can be moved forwardly and rearwardly during this procedure without disengaging the CSD 10 from the delivery device. Sub-xyphoid or other desired access approaches can be used for these minimally invasive delivery procedures.

When the CSD 10 is positioned at a desired location adjacent to the apex of the patient's heart, handle 120 is actuated to drive the deployment mechanism 106 to its extended state shown in FIG. 9. When in the extended state, the deployment mechanism 106 will open the base end 18 of the jacket 12. The delivery device 100 can then be further manipulated to slide the CSD 10 over the heart of the patient, and to position the CSD at the desired location on the heart. During this portion of the delivery procedure the opposite ends of the CSD 10 remain constrained on delivery device 100. The delivery device 100 can therefore be manipulated as needed to locate the CSD at the desired position (e.g. the delivery device can be moved forwardly, rearwardly and rotated, and corresponding motions transferred to the CSD). The presence of the lubricious members 34 between the epicardial surface of the patient's heart and the jacket 12 during this portion of the procedure reduces the friction between the heart surface and jacket, enabling the jacket to be more efficiently implanted.

The lubricious members 34 can be removed after the CSD 10 is positioned on the heart. In the embodiment of the invention described above, the lubricious members 34 are removed through the apex end 22 of the jacket 12 through the use of pull members 52. This action can be accomplished by the surgeon grasping the proximal end 56 of the pull members 52 and removing the pull members from the handle 120 (e.g., by disengaging the holes 142 from the pins 122). With continued motion of the pull members 52 in a direction generally away from the jacket 12 against the stabilizing force provided by the support members 118 of the deployment device 106 as described above in connection with FIGS. 3A and 3B-5A and 5B, the lubricious members 34 can be separated from the jacket 12 and both the lubricious members and the pull members withdrawn from the pericardial space and patient's body through the surgical access site. The relatively low friction surfaces of the lubricious members 34 and pull members 52 facilitate the removal of these structures from the implanted CSD 10 while minimizing disruptions of the CSD position on the patent's heart. Following the removal of the lubricious members 34, the handle 120 of the delivery device 100 is actuated to return the deployment mechanism 106 to the retracted state so it can be withdrawn through the surgical access site. The securing structure (e.g., elastic band 14) then functions to hold the CSD 10 on the heart. In other embodiments (not shown) the delivery device 100 can be withdrawn before the removal of the lubricious members 34.

Figure 12:
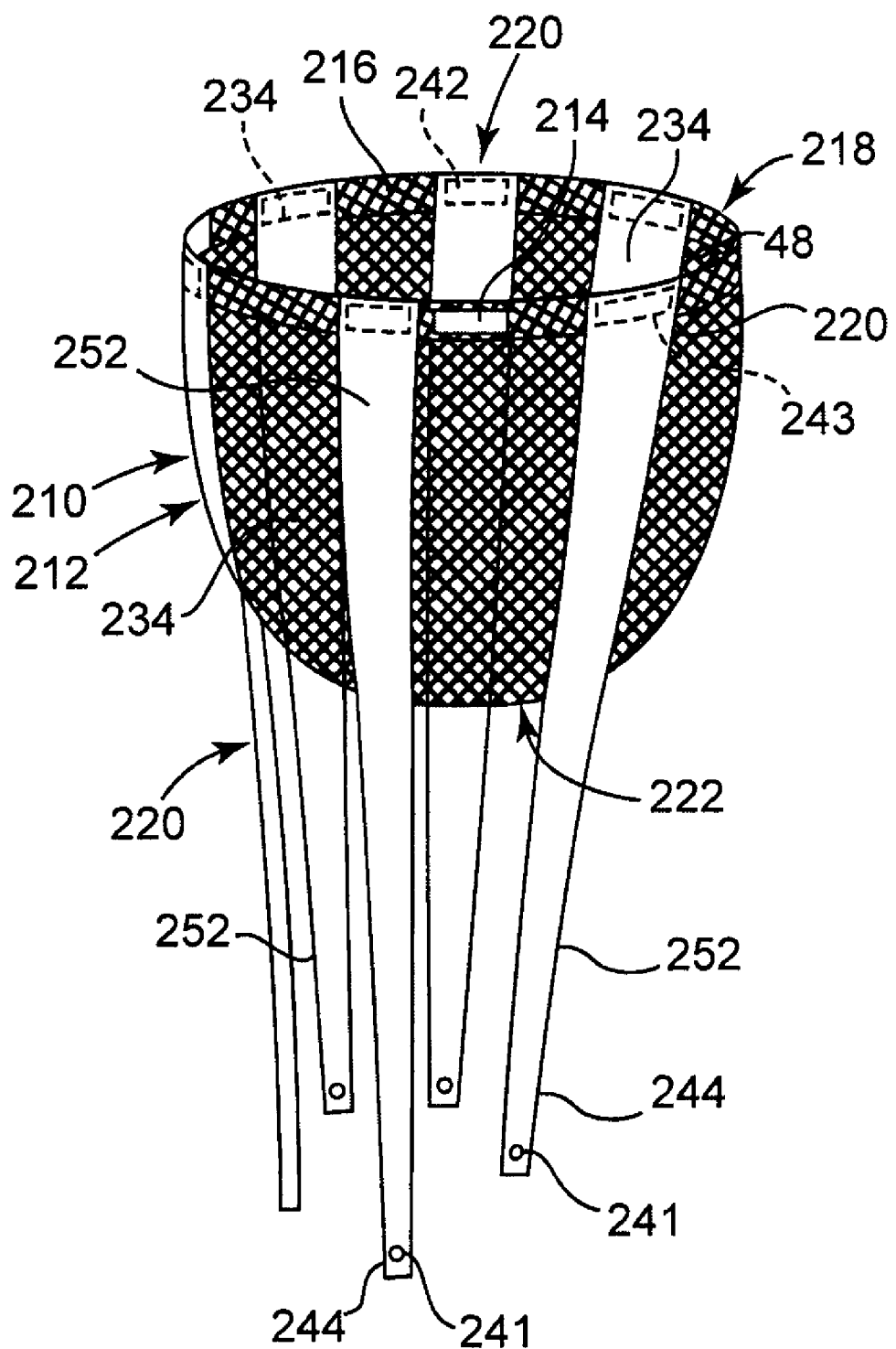
FIG. 12 is an isometric side view of a cardiac support device in accordance with a second embodiment of the invention.

FIG. 12 is an illustration of a cardiac support device (CSD) 210 in accordance with a second embodiment of the invention. CSD 210 includes a jacket 212, a self-adjusting securing structure in the form of an elastic band 214 in a hem 216 on a base end 218 of the jacket, and a plurality of lubricious element structures 220. Jacket 212 has a closed apex end 222 in this embodiment of the invention, and lubricious element structures 220 are configured to be removed from the open base end 218 of the jacket. Other than the closed apex end 222 and the features of lubricious element structures 220 described below, CSD 210 can be substantially the same as or similar to CSD 10 described above.

Lubricious element structures 220 include a lubricious member portion 234 and pull member portion 252. The lubricious member portions 234 are located on the inside surface of the jacket 212. In the illustrated embodiment the lubricious member portions 234 extend from the base end 218 of jacket 212 toward the apex end 222. The pull member portions 252 are connected to the lubricious member portions 234 over the base end 218 of jacket 212, and extend from the base end of the jacket 212 on the outside of the jacket. The lubricious member portions 234 are effectively releasably secured with respect to the jacket 212 by the interconnection with the pull member portions 252. Other embodiments of the invention (not shown) include other structures for releasably securing the lubricious member portions 234 to the jacket 212. In the illustrated embodiment the lubricious member portions 234 and pull member portions 252 are portions of a unitary strip of PTFE, with the strip folded over the base end 218 of the jacket 212. In other embodiments (not shown) the lubricious member portions 234 and pull member portions 252 can be different elements that are joined together. In still other embodiments (not shown), the lubricious member portions 234 and pull member portions 252 can be formed from different materials. In general, the lubricious member portions 234 and pull member portions 252 can be formed from the same materials as those of the lubricious members 34 and pull members 52 of CSD 10 described above.

CSD 210 can be implanted onto the heart of a patient using a delivery device 100 of the type described above in connection with FIGS. 6 and 7. For example, pockets 242 near the base end 218 of the CSD 210 can be used to engage the support members 118 of the deployment mechanism 106. The pockets 242 can, for example, be formed on the outside of the jacket 212 (e.g., on the hem 216) or on the pull members portions 252. Holes 241 on the proximal portions 244 of the pull member portions 252 can be used to releasably engage the pull member portions to the handle 120 of the delivery device 100. The CSD 210 can be loaded onto the delivery device 100 with the support members 118 on the outside of the jacket 212 (e.g., between the jacket and the pull member portions 252). When the delivery device 100 loaded with the CSD 210 (not shown) is in the retracted state, the CSD can be completely or partially withdrawn into the distal end 105 of the body 104, with the pull member portions 252 extending along the outside of the body 104. Other structures and approaches (not shown) can also be used to releasably secure the proximal portions 244 of the pull members portions 252 to the delivery device 100.

The delivery device 100 loaded with the CSD 210 as described above can be inserted into the patient's pericardial space, deployed to the extended state and the CSD positioned on the patient's heart in a manner similar to that described above in connection with CSD 10. After the CSD 210 is properly located on the patient's heart, the pull member portions 252 can be grasped by the surgeon, released from the handle 120, and pulled in a direction generally away from the CSD to remove the lubricious member portions 234 from between the jacket 212 and the heart. Specifically, by pulling the pull member portions 252, the lubricious member portions 234 are pulled over the base end 218 of the jacket 212. The support members 118 of the delivery device 106 can provide support to enable the lubricious member portions 234 to be removed in the matter described above. In other embodiments (not shown), friction reducing members or structures such as rollers or rounded surfaces on the distal portions 119 of the support members 118 can be configured to be located adjacent to the lubricious member portions 234 to enhance the ability of the lubricious member portions to be removed by the action of the pull member portions 252. In still other embodiments (also not shown), the delivery device can include additional stages or structures (e.g., another set of members such as the support members 118) that provide support enabling the lubricious member portions 234 to be removed. After the lubricious member portions 234 (and the pull member portions 252) are removed from the patient, the delivery device 100 can be removed in the manner described above in connection with CSD 10. Lubricious member portions 234 provide friction-reducing advantages similar to those described above in connection with CSD 10 during the implantation of the CSD 210 on a patient's heart.

Figure 13:
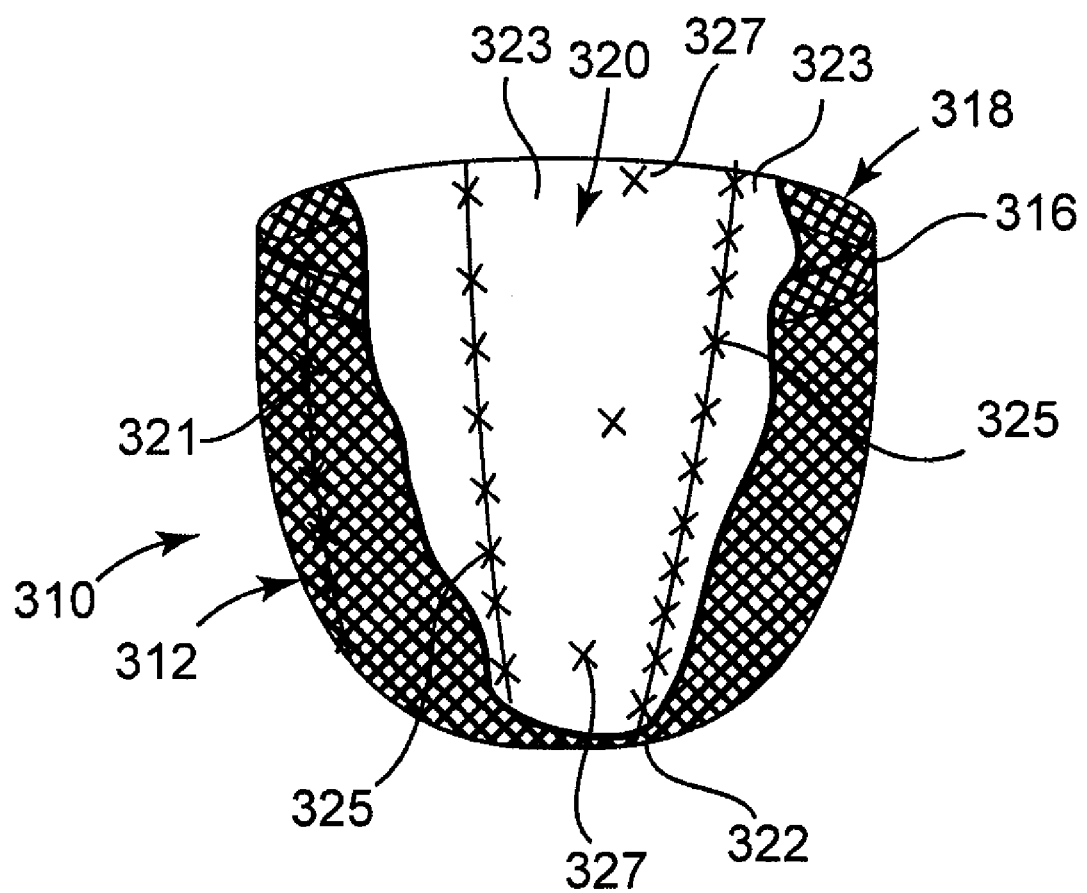
FIG. 13 is an isometric side view, with portions thereof broken away, of a cardiac support device in accordance with a third embodiment of the invention.

FIG. 13 is an illustration of a cardiac support device (CSD) 310 in accordance with a third embodiment of the invention. CSD 310 includes a jacket 312, a hem 316 on a base end 318 of the jacket, a hem 321 extending between the base end and the apex end 322, and a lubricious member 320. Jacket 312 has a closed apex end 322, and does not include a self-adjusting securing structure in this embodiment of the invention. CSD 310 is configured to be implanted on a patient's heart through conventional open-chest procedures (e.g., through a sternotomy). Other than the differences described herein, including those of the lubricious member 320, CSD 310 can be substantially the same as or similar to CSD 10 described above.

Lubricious member 320 is a cup-shaped member having a shape corresponding to the interior surface of the jacket 312. In the embodiment shown, the lubricious member 320 is formed from a plurality of sections 323 attached to one another by structures such as stitches 325. The lubricious member 320 can be formed from the same materials as those of lubricious members 34 of CSD 10 described above. Stitches such as those shown at 327 can be used to releasably secure the lubricious member 320 to the jacket 312. Although the illustrated embodiment of lubricious member 320 is a unitary member that lines substantially the entire inside surface of jacket 312, other embodiments (not shown) cover lesser portions of the jacket, or include a plurality or individual and separate sections that together line substantially all or lesser portions of the inside surface of the jacket. Other structures (not shown) such as adhesives can be used to releasably secure the lubricious member 320 or its sections to the jacket 312. In still other embodiments (not shown) the lubricious member 320 is not releasably attached to the jacket 312.

During implantation, a surgeon can by hand slide the CSD 310 over the patient's heart. After the CSD 310 is located, the surgeon can open the jacket 312 and manually (e.g., by hand or through the use of an instrument) remove the lubricious member 320. For example, the hem 321 can be opened between the base end 318 and apex end 322 of the jacket 312, and the lubricious member 320 withdrawn through that opening. If necessary, any structures releasably securing the lubricious member 320 to the jacket 312 can be removed (e.g., stitches 327 can be cut). Following the removal of the lubricious member 310, the opening in the jacket 312 is closed (e.g., by restitching the hem 321). By this closure procedure the jacket 312 can be properly sized and fit onto the heart. Other structures or methods can also be used to open and close the jacket 312 after it has been initially placed on the patent's heart. Use of the lubricious member 320 enhances the efficiency by which the jacket 312 can be implanted during the surgical procedure.

Figure 14:
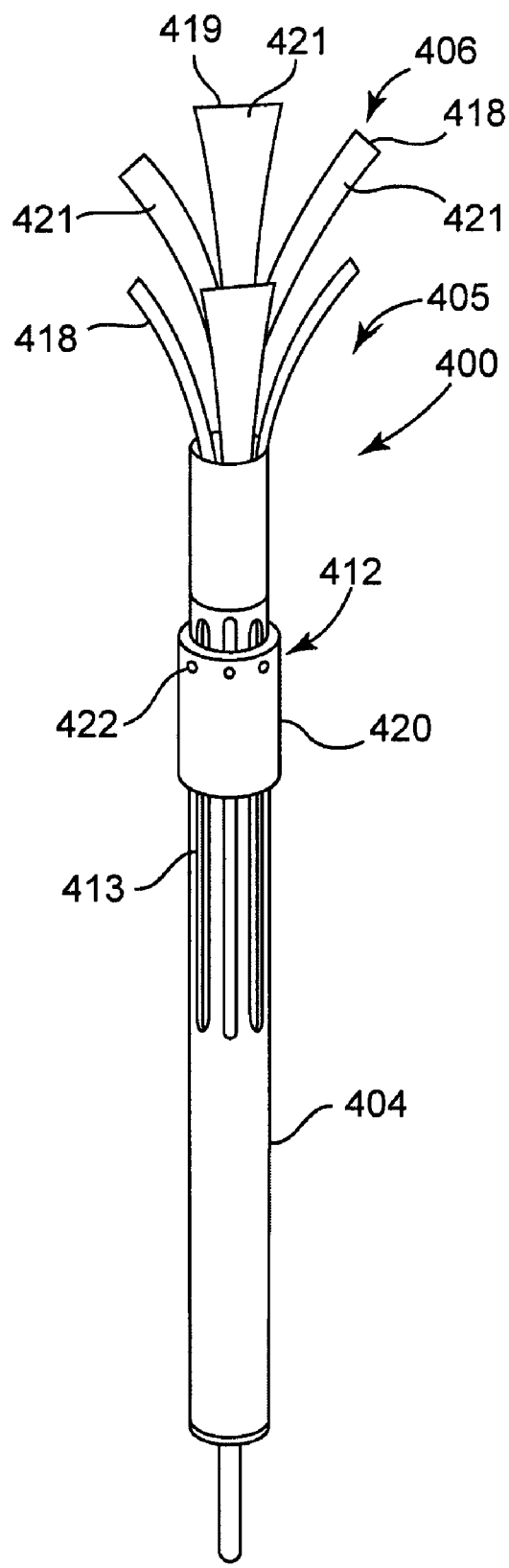
FIG. 14 is an isometric view of a delivery device in accordance with another embodiment of the invention, shown in an extended state.

FIG. 14 is an illustration of a delivery device 400 in accordance with another embodiment of the invention. Delivery device 400 can be used to deliver and deploy a conventional or otherwise known CSD including, but not limited to, those described in this document and the patents and patent applications identified above and incorporated herein. In one embodiment, delivery device 400 can be used to deliver a CSD that is free from lubricious structures such as 20, 220 and 320, while still providing the efficient, low-friction delivery advantages of the other embodiments of the invention described herein.

As shown, delivery device 400 includes a body 404 having a distal end 405, a deployment mechanism 406 having lubricious support members 418, and an actuating mechanism 412. The body 404 is a generally tubular member, and includes a plurality of elongated slots 413 extending through the body at a location adjacent to the actuating mechanism 412. Actuating mechanism 412 includes a handle 420 that is slidably mounted to the body 404. Structures such as pins 422 on the handle 420 extend into the slots 413. Deployment mechanism 406 includes a plurality (six are shown) of lubricious support members 418 within the body 404. Proximal ends of the support members 418 are connected to the pins 422 within the body 404. The distal portions 419 of the lubricious support members 418 are located near the distal end 405 of the body 404. Other embodiments of delivery device 400 (not shown) can include different or additional structures including, for example, a suction cup or other structures on the distal end 405 of body 404 for engaging the heart during the use of the device.

Handle 420 is actuated to drive the deployment mechanism 406 between a first retracted or closed state (not shown) and a second extended or open state shown in FIG. 14. In the retracted state, the lubricious support members 418 are in a reduced-diameter configuration (similar to that of the embodiment shown in FIG. 6). In the illustrated embodiment this configuration is achieved by the handle 420 withdrawing at least portions of the lubricious support members 418 into the distal end 405 of the body 404. Distal end portions 419 of the lubricious support members 418 extend from the body 404 in some embodiments of the invention when the deployment mechanism 406 is in the retracted state. in other embodiments (not shown), the support members 418 are not enclosed within the body 404 when in the retracted state. When the handle 420 is slid toward the distal end 405 of the body 404, the lubricious support members 418 are driven to the extended state shown in FIG. 14 at which the distal ends 419 form an open array or enlarged-diameter configuration.

Lubricious support members 418 can be resilient structures formed from materials such as metals and polymers. The resilient nature of the support members 418 enables the members to move radially with respect to the body 404 during movement between the retracted and extended states. In some embodiments of the invention the support members 418 can also curve in a circumferential direction from a flat configuration to an arced configuration generally conforming to the shape of adjacent portions of the heart. At least portions of the interior surfaces 421 of the support members 418 (i.e., the surfaces that will be adjacent or in contact with the heart during CSD delivery) are lubricious. The lubricious support members 418 can, for example, be formed from the materials of lubricious elements 34 described above, or from the materials of the support members 118 of delivery device 100 described above. In embodiments having lubricious support members 418 including materials that are not lubricious, coatings of lubricious materials such as those described above in connection with lubricious elements 34 can be applied to all or portions of the non-lubricious portions of the support members 418.

In the embodiment shown in FIG. 14 the lubricious support members 418 have greater surface area than the support members 118 of delivery device 100 described above, thereby enhancing the friction-reducing characteristics of the support members. The lubricious support members 418 are generally paddle-shaped in that they have a relatively large surface area, with substantial surface portions of the members having a width that is substantially greater than the thickness of the members. The amount of lubricious surface on the support members 418 is sufficient or effective to enable the delivery device 400 to substantially reduce the amount of friction that would otherwise be present between a CSD and heart during delivery, and thereby enable the efficient positioning of the CSD. The lubricious support members 418 have other shapes and sizes in other embodiments of the invention (not shown). In general, the greater the amounts of lubricious surface area on the support members 418, the greater the efficiency of the delivery device 400.

Delivery device 400 can be used and operated in a manner similar to that of delivery device 100 described above to deliver and deploy a CSD on a patient's heart. As noted above, the CSD used in connection with delivery device 400 need not, however, include lubricious element structures such as 20, 220 and 320 described above in connection with other embodiments of the invention, since the lubricious support members 418 can provide sufficient friction reduction. Briefly, the CSD (not shown) can be releasably attached at its base end to the distal ends 419 of lubricious support members 418, with the support members 418 on the inside surface of the CSD jacket extending through an open apex. Any conventional or otherwise known releasable attachment structure, including but not limited to those described in the patents and applications incorporated herein, can be used for this purpose. The delivery device 400 and attached CSD can, in the retracted state, have a configuration similar to that of delivery device 100 and CSD 10 shown and described in connection with FIG. 8. The delivery device 400 and CSD are inserted into the patient's pericardial space and manipulated into position adjacent to the heart in a manner similar to that of delivery device 100 described above. After the delivery device 400 is positioned at a desired location adjacent to the apex of the patient's heart, handle 420 is actuated to drive the deployment mechanism 406 to its extended state shown in FIG. 14. When in the extended state, the deployment mechanism 406 will open the base end of the jacket and have a configuration similar to that of delivery device 100 and CSD 10 shown and described in connection with FIG. 9. The delivery device 400 and CSD can then be further manipulated to slide the CSD over the patient's heart and to position the CSD at the desired location on the heart. The CSD can then be detached from the deployment mechanism 406, and the delivery device 400 withdrawn from the surgical access site. The presence of the lubricious support members 418 between the epicardial surface of the patient's heart and the CSD jacket reduces the friction between the heart surface and jacket, enabling the CSD to be more efficiently implanted.

Although the present invention has been described with reference to preferred embodiments, those skilled in the art will recognize that changes can be made in form and detail without departing from the spirit and scope of the invention. For example, in yet another embodiment of the invention, lubricious material is positioned on the surface of the heart before the CSD is positioned on the heart. The lubricious material is then removed (e.g., through the base or an open apex of the CSD) after the device is positioned.

What is claimed is:

1. An assembly including a cardiac support device and delivery device, the assembly comprising:
    a delivery device including:
        a body,
        a deployment mechanism movable between retracted and extended states with respect to the body, and
        an actuating mechanism for moving the deployment mechanism between the retracted and extended states;
    a cardiac support device releasably attached to the deployment mechanism, including a jacket having an inside surface, open base portion and an apex portion;
    one or more lubricious elements releasably secured with respect to the inside surface of the jacket to reduce friction between the jacket and a heart when the cardiac support device is being positioned on the heart; and
    removal structure operatively connected to the lubricious elements to enable removal of at least portions of the one or more lubricious elements from between the jacket and the heart after the cardiac support device is positioned, without removing the cardiac support device from the heart.

2. The assembly of claim 1 wherein the one or more lubricious elements includes a plurality of lubricious elements at spaced locations around the inside of the jacket.

3. The assembly of claim 2 wherein the one or more lubricious elements are releasably secured to the jacket at the base portion.

4. The assembly of claim 1 wherein the one or more lubricious elements includes a single unitary lubricious element.

5. The assembly of claim 1 wherein:
    the one or more lubricious elements includes a plurality of lubricious elements at spaced locations around the inside of the jacket; and
    the removal structure further includes one or more pull members connected to the lubricious elements.

6. The assembly of claim 5 wherein the pull members are formed from lubricious material.

7. The assembly of claim 5 wherein the pull members are releasably connected to the actuating mechanism of the delivery device.

8. The assembly of claim 1 wherein:
    the jacket has an open apex; and
    the deployment mechanism extends through the open apex.

9. The assembly of claim 8 wherein:
    the one or more lubricious elements includes a plurality of lubricious elements at spaced locations around the inside of the jacket; and
    the removal structure further includes one or more pull members connected to the lubricious elements and extending through the open apex of the jacket.

10. The assembly of claim 9 wherein the pull members are formed from lubricious material.

11. The assembly of claim 9 wherein portions of the pull members are connected to the actuating mechanism of the delivery device.

12. The assembly of claim 1 wherein at least portions of the deployment mechanism within the jacket have a lubricious surface.

13. The assembly of claim 1 wherein the removal structure includes one or more pull members connected to the one or more lubricious elements.

14. The assembly of claim 13 wherein:
    the removal structure includes a weakened structure on the one or more lubricious elements; and
    the pull members are connected to the lubricious elements at the weakened structure.

15. The assembly of claim 1 wherein the one or more lubricious elements are releasably secured to the jacket.

16. The assembly of claim 1 wherein the deployment mechanism includes a plurality of spaced-apart support members having a lubricious surface extending from the body, 17. The assembly of claim 16 wherein the support members extend from the body of the delivery device inside the jacket.

18. The assembly of claim 17 wherein the support members have sufficiently large lubricious surfaces to substantially reduce friction between the jacket and a heart onto which the jacket is being positioned to enable the efficient positioning of the jacket onto the heart.

19. The assembly of claim 18 wherein the support members have a width and a thickness, and wherein the width of at least substantial portions of the members is substantially greater than the thickness of the members.

* * * * *